United States Patent [19]
Kozlowski et al.

[11] Patent Number: 6,096,499
[45] Date of Patent: Aug. 1, 2000

[54] MAMMALIAN DNA PRIMASE SCREEN AND ACTIVITY MODULATING AGENTS

[75] Inventors: Michael Kozlowski, Palo Alto; Junko Aimi, San Carlos, both of Calif.

[73] Assignee: Geron Corporation, Menlo Park, Calif.

[21] Appl. No.: 08/828,192

[22] Filed: Mar. 21, 1997

Related U.S. Application Data

[63] Continuation-in-part of application No. 08/624,343, Mar. 22, 1996, abandoned.

[51] Int. Cl.$^7$ ...................................................... C12Q 1/68
[52] U.S. Cl. .................................. 435/6; 435/15; 435/18; 435/29; 435/32; 435/69.1; 435/91.1; 514/2; 514/44
[58] Field of Search ............................. 435/6, 8, 10, 15, 435/18, 29, 32, 69.1, 91.1; 436/501; 514/2, 44; 536/23.1, 24.1, 24.3–33; 935/77, 78

[56] References Cited

U.S. PATENT DOCUMENTS 5,360,714  11/1994  Seeger ........................................... 435/5
5,677,152  10/1997  Birch et al. ............................. 435/91.2

FOREIGN PATENT DOCUMENTS

WO90/00624  1/1990  WIPO ............................... C12Q 1/68

OTHER PUBLICATIONS

Reiter et al., European Journal of Biochemistry, vol. 164, pp. 59–63, 1987.

Gronostajski et al. (1984) Journal of Biological Chemistry, vol. 259, No. 15, pp. 9479–9486.

Matthews et al. (1988) Analytical Biochemistry, vol. 169, pp. 1–25.

Bruckner et al. (1995), "The mouse DNA polymerase α–primase subunit p48 mediates species–specific replication of polyomavirus DNA in vitro," *Mol. Cell. Biol.* 15:1716–1724.

Copeland and Wang (1993), "Enzymatic characterization of the individual mammalian primase subunits reveals a biphasic mechanism for initiation of DNA replication," *J. Biol. Chem.* 268:26179–26189.

Copeland and Tan (1995), "Active site mapping of the catalytic mouse primase subunit by alanine scanning mutagenesis," *J. Biol. Chem.* 270:3905–3913.

Kuchta et al. (1990), "DNA Primase," *J. Biol. Chem.* 265:16158–16165.

Kuchta et al. (1992), "Inhibition of DNA primase and Polymerase α by arabinofuranosylnucleoside triphosphates and related compounds," *Biochemistry* 31:4720–4728.

Miyazawa et al. (1993), "Molecular cloning of the cDNAs for the four subunits of mouse DNA polymerase α–primase complex and their gene expression during cell proliferation and the cell cycle," *J. Biol. Chem.* 268:8111–8122.

Prussak et al. (1989), "Mouse primase p49 subunit molecular cloning indicates conserved and divergent regions," *J. Biol. Chem.* 264:4957–4963.

Santocanale et al. (1992), "Overproduction and functional analysis of DNA primase subunits from yeast and mouse," *Gene* 113:199–205.

Stadlbauer et al. (1994), "DNA replication in vitro by recombinant DNA–polymerase–α–primase," *Eur. J. Biochem.* 222:781–793.

Stillman (1989), "Initiation of eukaryotic DNA replication in vitro," *Ann. Rev. Cell. Biol.* 5:197–245.

(List continued on next page.)

*Primary Examiner*—Ardin H. Marschel
*Attorney, Agent, or Firm*—David J. Earp

[57] ABSTRACT

The invention provides DNA primase assays suitable for identifying DNA primase modulating agents, methods of modulating DNA primase activity and compositions which modulate DNA primase.

12 Claims, 4 Drawing Sheets

| $IC_{50}$ (μM) | Structure | $IC_{50}$ (μM) | Structure | $IC_{50}$ (μM) | Structure |
|---|---|---|---|---|---|
| 55 | PRIMASE MODULATOR 1 | 49 | PRIMASE MODULATOR 2 | 72 | PRIMASE MODULATOR 3 |
| 30 | PRIMASE MODULATOR 4 | 25 | PRIMASE MODULATOR 5 | 35 | PRIMASE MODULATOR 6 |
| 77 | PRIMASE MODULATOR 7 | 31 | PRIMASE MODULATOR 8 | 46 | PRIMASE MODULATOR 9 |

OTHER PUBLICATIONS

Thompson and Kuchta (1995), Arabinofuranosyl nucleotides are not chain–terminators during initiation of new strands of DNA by DNA polymerase α–primase, *Biochemistry* 34:11198–11203.

Waga and Stillman (1994), "Anatomy of a DNA replication fork revealed by reconstitution of SV40 DNA replication in vitro," *Nature* 369:207–212.

Wang (1991), "Eukaryotic DNA polymerases," *Ann. Rev. Biochem.* 60:513–552.

Catapano, C.V., et al., Inhibition of Primer RNA Formation in CCRF–CEM Leukemia Cells by Fludarabine Triphosphate, Cancer Res., Apr. 1, 1991, vol. 51, No. 7, pp. 1829–1835.

Sheaff, R.J. calf Thymus DNA Polymerase Alpha–Primase: "Communication" and Primer–Template Movement Between the Two Active Site, Biochemistry, 1994, vol. 33, No. 8, pp. 2247–2254.

FIG. 1A

| Structure | IC$_{50}$ (μM) | Structure | IC$_{50}$ (μM) | Structure | IC$_{50}$ (μM) |
|---|---|---|---|---|---|
| PRIMASE MODULATOR 1 | 55 | PRIMASE MODULATOR 2 | 49 | PRIMASE MODULATOR 3 | 72 |
| PRIMASE MODULATOR 4 | 30 | PRIMASE MODULATOR 5 | 25 | PRIMASE MODULATOR 6 | 35 |
| PRIMASE MODULATOR 7 | 77 | PRIMASE MODULATOR 8 | 31 | PRIMASE MODULATOR 9 | 46 |

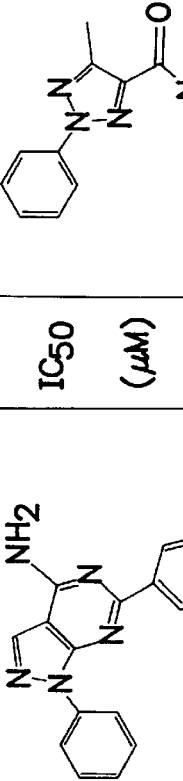
FIG. IB

| IC$_{50}$ ($\mu$M) 58 | PRIMASE MODULATOR 19 | IC$_{50}$ ($\mu$M) 37 | PRIMASE MODULATOR 20 |
|---|---|---|---|
| IC$_{50}$ ($\mu$M) 45 | PRIMASE MODULATOR 21 | IC$_{50}$ ($\mu$M) | PRIMASE MODULATOR 22 |

FIG. IC

PRIMASE MODULATOR 24
(20 μM)

PRIMASE MODULATOR 25
(75 μM)

PRIMASE MODULATOR 17
(72 μM)

PRIMASE MODULATOR 20
(37 μM)

PRIMASE MODULATOR 23
(10 μM)

MAMMALIAN DNA PRIMASE SCREEN AND ACTIVITY MODULATING AGENTS

CROSS REFERENCE TO RELATED APPLICATIONS

This application is a continuation-in-part of U.S. patent application Ser. No. 08/624,343 by Kozlowski, filed Mar. 22, 1996 (now abandoned), which is incorporated herein by reference for all purposes.

FIELD OF THE INVENTION

The invention relates to methods for identifying agents that modulate the catalytic activity and/or stability of mammalian DNA primase, compositions of such agents, improved DNA primase assay methods suitable for high-throughput screening to identify such agents, and the use of such methods to identify pharmaceutical agents and laboratory reagents which modify DNA primase activity.

BACKGROUND

DNA polymerase α and DNA primase are components of the DNA replication machinery, and play a role in the initiation of synthesis. In the double-stranded DNA of a chromosome, initiation occurs on both the leading and lagging strands, occurring more frequently on the lagging strand. The initiation of new DNA strands at origins of replication in animal cells involves the de novo synthesis of RNA primers by a primase activity and subsequent elongation of the RNA primers by one or more DNA polymerase activities, including that of DNA polymerase.

DNA primase initiates DNA replication by the synthesis of ribonucleotide primers which serve as a substrate for elongation by DNA polymerase α activity. The primase activity synthesizes short oligoribonucleotides during initiation of DNA replication and elongation of the lagging strand. DNA polymerase α elongates the RNA primer to complete the synthesis of the Okazaki fragment (Stillman B (1989) *Ann. Rev. Cell. Biol.* 5: 197). Okazaki fragments are then extended by either DNA polymerase δ or ε, allowing DNA polymerase α and DNA primase to recycle and initiate another Okazaki fragment on the lagging strand (Waga S and Stillman B (1994) *Nature* 369: 207). This essential role of DNA primase makes it a key component in the regulation of initiation of DNA replication. A general overview of eukaryotic DNA replication is provided in Wang T S F (1991) *Ann. Rev. Biochem.* 60: 513.

A unique property of DNA primase (as well as RNA polymerase) is the ability to synthesize oligonucleotides de novo on a template by the formation of an initial dinucleotide. DNA primase initiates synthesis with a triphosphate purine moiety at the 5' end (Gronostajski et al. (1984) *J. Biol. Chem.* 259: 9479). After synthesis of 7–10 ribonucleotides, the primer template is translocated intramolecularly to the active site of lie DNA polymerase α subunit.

Mammalian DNA primase and DNA polymerase α copurify as a complex containing four subunits with approximate molecular masses of 180, 68, 58, and 49 kD. The 58 kD (p58) and 49 kD (p49) subunits can be separated from the 180 kD (p180) and 68 kD (p68) subunits and retain DNA primase activity when present as a p49–p58 complex. Thus, the p49 and p58 polypeptides are conventionally referred to in the art as the small subunit and large subunit of DNA primase, respectively.

The large and small subunits of DNA primase have been cloned as cDNA from mouse (Prussak et al. (1989) *J. Biol. Chem.* 264: 4957; Stadlbauer et al. (1994) *Eur. J. Biochem.* 222: 781; Miyazawa et al. (1993) *J. Biol. Chem.* 268: 8111) and human (Stadlbauer et al. (1994) op.cit; Miyazawa et al. (1993) op.cit) and the sequences of the genes, gene products, coding nucleic acids and corresponding amino acid sequences of the proteins are reported in the EMBL/GenBank computer-accessible public databases, among others. Enzymatically active DNA primase has been produced from recombinant expression constructs in baculovirus-infected insect cells, yeast cells, and in *E. coli* cells (Bruckner et al. (1995) *Mol. Cell. Biol.* 15: 1716; Copeland W C and Wang T S F (1993) *J. Biol. Chem.* 268: 26179; Santocanale et al. (1992) *Gene* 113: 199). Alanine scanning mutagenesis has been performed to localize the catalytic site of the small subunit of mouse DNA primase (Copeland W C and Tan X (1995) *J. Biol. Chem.* 270: 3905).

The pharmaceutical sciences have identified agents which inhibit eukaryotic DNA replication at one or more steps. DNA replication inhibitory agents are used as human and veterinary drugs, such as antineoplastic agents (e.g., arabinosylcytosine, thioguanine, 5-fluorouracil, hydroxyurea, mitomycin, daunorubicin, doxyrubicin, actinomycin D, cyclophosphamide, etc.), antiviral agents (e.g., AZT, 3TC, ddI, acyclovir, gancyclovir, foscarnet, etc.), antifungal agents, and the like. Identification and development of new modulators of DNA replication and/or DNA repair synthesis provide new, improved, and/or alternative pharmaceuticals to treat diseases such as cancer, viral diseases (e.g., hepatitis B, AIDS), and other pathological conditions.

Arabinofuranosyl nucleotides have been reported to inhibit DNA synthesis by acting as chain terminators of elongation by DNA polymerase α. These same nucleotide "chain terminator" compounds have been reported to be incorporated by DNA primase and not result in chain termination (Thompson H C and Kuchta R D (1995) *Biochemistry* 34: 11198; Kuchta et al. (1992) *Biochemistry* 31: 4720). Thus, compounds which are known chain terminators of DNA polymerases are not necessarily chain terminators of DNA primase.

It would be advantageous to have a method for identifying agents which produce a decrease or, alternatively, an increase in mammalian DNA primase activity. Such DNA primase modulators could serve as candidate pharmaceutical agents to treat a variety of diseases, as well as laboratory reagents, for example as controls in a screen for primase activity, or for agents that modulate primase activity. Because of the large number of potential agents which can be screened for the activity of modulating DNA primase activity, it would be desirable if such a method were suitable for high-throughput screening of compound libraries. It would also be desirable to obtain compositions of specific DNA primase modulators, particularly agents which selectively modify DNA primase activity as compared to any effects on other enzymes involved in DNA metabolism (e.g., DNA polymerase (α, β, γ, δ, ε), helicase or telomerase) and/or RNA metabolism (e.g., RNA polymerase (pol I, pol II, pol III) and related proteins). As many current DNA synthesis/replication inhibitors are nucleotides, nucleosides, and analogs thereof, and much scrutiny is directed at developing this class of agents, it would be desirable to have a method suitable for identifying DNA primase modifiers which are compounds other than, or in addition to nucleotides or nucleosides.

The present invention fulfills these and other needs, and provides methods which will find wide applicability in the art.

SUMMARY OF THE INVENTION

The present invention provides new methods for identifying agents that modulate mammalian DNA primase activity. Although described herein with reference to mammalian DNA primases, such as human DNA primases, the method can be suitably adapted by those skilled in the art for identifying modifiers of non-human (e.g., murine) DNA primases as well. The method can be practiced with reference to DNA primase activity associated with DNA polymerase α, primase activity associated with other DNA polymerases, or primase activity associated with any mammalian telomerase. Such adaptations will be apparent to those skilled in the art in view of the present disclosure of the general method and specific embodiments provided.

The present invention provides compositions and methods for screening for agents which are modulators of one or more functions of mammalian DNA primase or its activity and agents which can modulate DNA primase-mediated cell replication and/or modulate neoplastic and immune conditions, as well as other pathological conditions dependent upon DNA primase function or activity.

In one aspect, the invention provides methods for identifying agents which modulate a mammalian DNA primase activity. An example of primase activity, or function, is the synthesis of a primer, optionally followed by polymerase elongation of the primer to create a complement to a template nucleic acid. A second example of primase activity is the direct or indirect binding of primase to a second molecule, such as a polymerase, an antibody, or the like. In such methods, a composition comprising a mammalian DNA primase enzyme is provided. The enzyme is optionally from a purified or partially purified natural source, or is optionally a recombinantly produced enzyme. The primase enzyme optionally comprises a moiety which is unrelated to a native primase enzyme; one such enzyme is a recombinant fusion protein comprising a primase domain and a second domain (e.g., in a two-hybrid system).

Example compositions comprising the primase enzyme include in vitro aqueous reaction mixtures, cells and organisms. The composition is contacted with the agent and the activity of the primase enzyme in the presence of the agent is monitored. This agent is optionally added to an in vitro reaction mixture, or a cell or the like which comprises the primase enzyme, wherein the activity in the presence of the agent is an indicator for whether the agent modulates primase activity.

In many embodiments, the activity of the primase enzyme is monitored by measuring incorporation of a nucleotide label into a nucleic acid polymer, for which primase initiated or primed synthesis. Alternatively, the activity of the primase enzyme can be monitored by measuring the binding of the enzyme to a polymerase protein or substrate.

Typically, the methods of the invention can include a control reaction in which the activity of the primase enzyme in the absence of the agent (or the presence of a control agent which modulates activity in a known way) is monitored and compared to the activity of the primase enzyme in the presence of the agent. Alternatively, a control reaction can be omitted, as for example, when a large preparation of primase with a known activity is available. Multiple assays are preferably performed in parallel in the methods of the invention, with several agents and/or several activities being screened simultaneously, a decided advantage if large numbers of the agents are to be screened.

Nucleic acids produced as a result of primase activity include DNA and RNA polymers. These polymers can be produced by the action of primase alone, or by the combined action of primase and a polymerase such as polymerase α. The production of a nucleic acid as a result of primase activity provides a measure of primase function for the primase enzyme. Nucleic acid production is typically measured by monitoring incorporation of labeled nucleic acids into the nucleic acid polymer, or by hybridizing a probe to the polymer, or by measuring total DNA or the amount of duplexed or single stranded products.

In one assay of the invention, a probe is hybridized to a primase reaction product, with the amount of probe bound providing a measure of activity for the primase enzyme. In one typical format, the probe or product is immobilized or captured on a solid surface, which is optionally washed to remove non-specifically bound components after hybridization with primase reaction products or probes to the products. Optionally, the assay includes a blocking agent, such as albumin, a nonfat milk protein, polyvinyl pyrrolidone, or Ficoll.

This invention further provides methods of modulating the activity of a mammalian primase. In these methods, an agent identified using an assay of the invention is contacted to a composition which includes the primase molecule. The agent then potentiates or inhibits the activity of the primase enzyme. Example inhibitors include Primase modulators 1–25, the structure of which are shown in FIG. 1. Examples of Preferred modulators include primase modulators 17, 19 and 20.

The present invention also provides compositions. These compositions include agents identified using an assay of the invention. These agents are identified, for example, when they are purified from mixtures used as agents in the screening assays of the invention, including combinatorial chemical libraries, cellular extracts and the like. In a preferred embodiment, the compositions comprises a primase molecule. For example, in one embodiment, the invention provides a composition in which an agent is bound, permanently or transiently, to the primase molecule which the agent modulates.

In an aspect, the invention provides methods for identifying DNA primase modulators or modifiers, such as a DNA primase inhibitor or DNA primase activator or potentiator. The method identifies DNA primase modifiers which produce: (1) a detectable alteration in DNA primase activity, such as the capacity of a DNA primase to initiate oligoribonucleotide primer synthesis and/or the rate of chain elongation of a nascent oligoribonucleotide primer catalyzed by DNA primase, either alone or in conjunction with a DNA polymerase (e.g., DNA polymerase α), and/or (2) a detectable alteration in the capacity or rate of a DNA primase/ DNA polymerase complex (e.g., DNA primase functionally bound to DNA polymerase α) to extend oligoribonucleotide primers by template-directed addition of deoxyribonucleotides (dNTPs), and/or (3) a detectable alteration in the binding capacity, binding affinity, or functional interaction between a DNA primase and an accessory protein, such as a DNA polymerase (e.g., DNA polymerase α). Thus, DNA primase modifiers can alter the catalytic activity of DNA primase and/or the binding of DNA primase to at least one predetermined binding partner (e.g., DNA polymerase α).

In an embodiment, the method comprises identifying as candidate DNA primase modifiers those agents which modulate primase activity. In the methods, the modifier is added to a DNA primase reaction comprising: (1) an enzymatically active DNA primase, (2) a suitable primase template polynucleotide, and (3) a primase reaction mixture containing at least one species of labeled nucleotide capable of being incorporated into a product polynucleotide chain (e.g., such as a dinucleotide or longer polynucleotide) by the catalytic activity of DNA primase, result in a detectable and reproducible increase or decrease in the amount of product polynucleotide produced in the reaction as compared to a standard or control reaction which is substantially identical except which lacks an added agent. In an embodiment, the DNA primase is a human or mouse DNA primase composed of large and small subunits obtained by expression of an encoding recombinant polynucleotide expression construct. In variations, the DNA primase subunit(s) can be expressed in prokaryotic or eukaryotic expression systems. In an embodiment, the primase template polynucleotide is a single-stranded DNA molecule; in a variation, the ssDNA template comprises the sequence 5'-GCTTTCTTC-3' (SEQ ID NO:1) or 5'-GCTTTCTTCC-3' (SEQ ID NO:2). In an alternative embodiment, the primase template polynucleotide is a double-stranded DNA molecule having a portion which is non-complementary or looped out to form an open helix replication bubble suitable to serve as an initiation locus for DNA primase. In an embodiment, the labeled nucleotide is a biotinylated, fluorescently labeled, or radiolabeled ribonucleotide, such as can be made using appropriately labeled nucleoside triphosphate (NTP), e.g., ATP, GTP, CTP, UTP, TTP, ITP, or the like. In other embodiments where primase-linked DNA polymerase activity is being detected, one or more labeled deoxyribonucleotide species can be used; such as a biotinylated, fluorescently labeled, or radiolabeled deoxyribonucleotide, such as dATP, dGTP, dCTP, dTTP, dITP, or the like. In an embodiment, the amount of product polynucleotide is determined by contacting the reaction mixture, following a suitable incubation period, with a substrate which selectively immobilizes or binds to polynucleotides and which substantially does not immobilize or bind to mononucleotides or labelling reagents; one example of such a substrate is a charged membrane (e.g., a glass fiber filter such as the 2SC filter from Whatman, Nylon 66, nitrocellulose, DEAE paper or the like). Alternatively, reaction products can be chromatographed or electrophoresed (e.g., PAGE) to separate polynucleotide products from unincorporated nucleotides or other materials.

In a variation, the reaction further comprises a DNA polymerase activity, typically a mammalian DNA polymerase α, and reaction conditions suitable for catalytic activity of the DNA polymerase(s), such that product polynucleotides formed by the activity of the DNA primase may be extended further by the DNA polymerase, which can be useful to enhance or amplify the signal resulting from incorporation of labeled nucleotide into product polynucleotide. In such embodiments, one or more labeled dNTPs are also present in the reaction mixture, typically including each dNTP which would be present in a complementary strand of a template polynucleotide. In an embodiment, only one species of dNTP is labeled (e.g., $^{32}$P-α-dCTP or biotinylated dGTP). In an alternative embodiment, multiple species of dNTP are labeled, and in a variation all dNTP species are labeled. In general, the method employs a DNA primase and/or DNA primase/DNA polymerase reaction comprising: (1) a template polynucleotide capable of providing a template for a mammalian DNA primase; (2) a labeled nucleotide or polynucleotide species, and optionally (for heteronucleotide template sequences) unlabeled nucleotide species such that the reaction contains nucleotide species (either labeled and unlabeled) representing nucleotides which can be efficiently incorporated in a complementary strand to the template polynucleotide; (3) a predetermined amount of mammalian, preferably human, DNA primase and, optionally, a predetermined amount of a mammalian, preferably human, DNA polymerase (e.g., DNA pol α) in suitable reaction conditions (e.g., pH, ionic strength, ATP, temperature, metal ion concentration, etc.). The DNA primase reaction typically contains either: (1) at least one labeled ribonucleotide species, and optionally additional unlabeled ribonucleotide species necessary for synthesis of a complementary RNA strand to the template, for direct reporting of RNA synthesis as a measure of primase activity, or (2) at least one labeled deoxyribonucleotide species, and optionally additional unlabeled ribonucleotide species and deoxyribonucleotide species necessary for synthesis of a complementary strand to the template, for reporting of DNA synthesis which indirectly reports primase activity as RNA primer synthesis is necessary for initiation of DNA synthesis. In embodiments where labeled DNA synthesis is reported, reaction times can be shortened to reduce the average length of DNA chains synthesized and/or a DNA chain terminator nucleotide (such as, e.g., dideoxynucleotide: ddCTP, ddTTP, ddGTP, ddATP, ddITP, etc.) can be included in sufficient amount to reduce average DNA chain length which may be preferable to ensure that DNA synthesis is substantially proportional to RNA primer synthesis (and that the readout, whether by labeled RNA synthesis or labeled DNA synthesis, is representative or proportional to DNA primase activity in the reaction).

In variations of the method it is not necessary to include labeled nucleotides. In such variations, the product polynucleotide(s) generated by DNA primase and/or DNA polymerase activity(ies) are immobilized and detected by hybridization of a labeled complementary probe which specifically hybridizes to the product polynucleotide(s) and substantially does not hybridize to the template polynucleotide(s). In embodiments, the immobilized polynucleotides are bound to a solid substrate (e.g., Nylon 66, nitrocellulose, etc.), and may optionally be blocked to prevent non-specific binding (such as with a pre-hybridization solution as described supra. and/or washed to remove non-specifically bound probe.

In a variation, labeled nucleotides bear distinct labels to distinguish template versus non-template directed polymerization in a DNA primase reaction or coupled DNA primase/DNA polymerase reaction. A first labeled nucleotide species having a first label is incorporated in polynucleotides produced from template-directed polynucleotide synthesis, such as DNA primase-catalyzed oligoribonucleotide primer synthesis or DNA primase/DNA polymerase-catalyzed elongation of a oligoribonucleotide primer by template-directed polymerization. A second labeled nucleotide species having a second label which can be distinguished or discriminated (i.e., is separately detectable) from the first label of the first nucleotide species is incorporated substantially only in polynucleotides produced by untemplated polymerization. In this variation, a "nucleotide deficient template" serves as a primase template, and is a homopolymer or a heteropolymer polynucleotide composed of residues of two or three deoxyribonucleotide species (i.e., the template lacks at least one dNTP species) wherein at least one of said deoxyribonucleotide residues is a complement nucleotide of the first labeled nucleotide, and wherein none of said deoxyribonucleotide residues is a complement nucleotide of said second labeled nucleotide, whereby template-directed polynucleotide synthesis by DNA primase or DNA primase/DNA polymerase yields a product polynucleotide comprising an incorporated (i.e., polymerized) residue of said first labeled nucleotide species and substantially lacking incorporated residues of said second labeled nucleotide species (except for minor misincorporation errors inherent in polynucleotide polymerases). The second labeled polynucleotide species is complementary to a dNTP species which is not present in the nucleotide-deficient template, and therefore polynucleotide products of the reaction having incorporated second labeled nucleotide residues substantially represent reaction products generated by untemplated polymerization. The method employs a DNA primase and/or DNA primase/DNA polymerase reaction comprising: (1) a nucleotide-deficient template and substantially lacking other template species; (2) a first labeled nucleotide species and a second labeled nucleotide species, and optionally unlabeled nucleotide species such that the reaction contains nucleotide species (either labeled and unlabeled) representing nucleotides which can be efficiently incorporated in a complementary strand to the nucleotide-deficient template; (3) a predetermined amount of mammalian, preferably human, DNA primase and, optionally, a predetermined amount of a mammalian, preferably human, DNA polymerase (e.g., DNA pol $\alpha$) in suitable reaction conditions (e.g., pH, ionic strength, ATP, temperature, metal ion concentration, etc.). The DNA primase reaction typically contains a first and second labeled nucleotide species which are either both ribonucleotides or are both deoxyribonucleotides. In embodiments where labeled DNA synthesis is reported, reaction times can be shortened, as described supra, to reduce the average length of DNA chains synthesized and/or a DNA chain terminator nucleotide (dideoxynucleotide: ddCTP, ddTTP, ddGTP, ddATP, ddITP, etc.) is included in sufficient amount to reduce average DNA chain length such that DNA synthesis is substantially proportional to RNA primer synthesis (i.e., the readout, whether labeled RNA synthesis or labeled DNA synthesis, is representative or proportional to DNA primase activity in the reaction). Alternatively, or in combination, the product polynucleotide(s) can be detected by hybridization with a complementary strand probe polynucelotide which may be labeled and/or which may be immobilized and used to capture, by hybridization, a labeled product polynucelotide having sufficient complementarity to hybridize under suitable hybridization conditions.

In a variation, a labeled ribonucleotide species having a first label and a deoxyribonucleotide species labeled with a differentiable label (i.e., a differentiable label can be quantitatively distinguished from the first label by a conventional art-known technique are used to separately report DNA primase activity as labeled RNA and DNA polymerase activity as labeled DNA. In this embodiment, the DNA primase reaction comprises: (1) a template polynucleotide suitable for templating DNA primase activity; (2) a labeled ribonucleotide species comprising a first label (e.g., 32P-$\alpha$-CTP), and optionally other ribonucleotide species, either unlabeled or labeled with said first label, necessary for efficient synthesis of complementary strand RNA primers, and a labeled deoxyribonucleotide species comprising a second label (e.g., biotinylated dTTP), and optionally other deoxynucleotide species (dNTPs), either unlabeled or labeled with said second label, as necessary for efficient synthesis of complementary strand DNA sequences to the template; and (3) a mammalian, preferably human, DNA primase and a mammalian, preferably human, DNA polymerase (e.g., DNA pol $\alpha$) in suitable reaction conditions (e.g., pH, ionic strength, ATP, temperature, metal ion concentration, etc.). In this embodiment, detection of the amount or relative quantity of the first label incorporated into polynucleotides reports RNA primer synthesis (DNA primase activity) and detection of the amount or relative quantity of the second label incorporated into polynucleotides reports DNA synthesis (DNA polymerase activity), while the combined information can be useful in detecting various types of inhibitors or activators, as well as in other applications as described below.

Each of the various embodiments of a DNA primase or a DNA primase/DNA polymerase reaction described can be used to detect and/or quantitate DNA primase activity and/or DNA polymerase activity and/or coupled DNA primase/DNA polymerase activity in a sample. Such detection or quantitation of DNA primase and/or DNA polymerase activity has a variety of applications, including quality control assays for biopharmaceuticals and reagents (e.g., commercial polynucleotide or enzyme preparations; such as DNA pol $\alpha$, DNA primase, reverse transcriptase or the like. Such quality control assays are especially advantageous when the product is obtained from a source (e.g., cell) which has or is suspected of having a mammalian DNA primase and/or a mammalian DNA polymerase present as a potential contaminant or as a desired species.

Alternatively, in aspects of the invention, the method of the invention employs a DNA primase or a DNA primase/DNA polymerase reaction which includes a predetermined amount and/or a predetermined activity of a mammalian, preferably human, DNA primase and, optionally, a mammalian, preferably human, DNA polymerase (typically DNA pol $\alpha$). In these aspects, the method is used to identify DNA primase modulators and/or DNA polymerase modulators from a library, or bank, of agents, or to detect such a DNA primase modulator or DNA polymerase modulator in a quality control assay of a sample. In these aspects, a DNA primase modulator, when added in an effective concentration to a DNA primase reaction or a DNA primase/DNA polymerase reaction, produces a statistically significant increase or decrease in the amount of product polynucleotide (DNA, RNA, or both) produced in the reaction as compared to a standard or control reaction which is substantially identical except which lacks an added agent such as a DNA primase modulator. A preferred measure of statistical significance is two standard deviations from the mean, wherein an agent which, when added at a maximally effective concentration or amount, produces a mean increase or decrease in the amount or rate or formation of reaction product polynucleotide which is at least two standard deviations outside of the mean of a set of control reactions which are substantially identical except lacking the agent. Active agents which reduce DNA primase activity are thereby identified and are termed herein as DNA primase inhibitors. Active agents which increase DNA primase activity are thereby identified and are termed DNA primase potentiators.

In embodiments where DNA synthesis is reported separately from RNA primer synthesis in the DNA primase/DNA polymerase reactions, it is possible to employ the method to identify agents which selectively or preferentially inhibit or potentiate DNA primase activity as compared to their effect, if any, on DNA polymerase activity. Thus, an agent which significantly inhibits DNA primase activity as reported by, for example, RNA primer synthesis (e.g., as reported by incorporation of labeled ribonucleotide into polynucleotide) but which has substantially less capacity to inhibit DNA polymerase-catalyzed elongation of DNA chains from the RNA primers (e.g., as reported by incorporation of labeled deoxyribonucleotide into polynucleotide) relative to the amount of RNA primer formation, is thereby identified as a selective DNA primase inhibitor. Similarly, an agent which significantly increases DNA primase activity as reported by RNA primer synthesis (e.g., as reported by incorporation of labeled ribonucleotide into polynucleotide) but which has substantially less capacity to increase DNA polymerase-catalyzed elongation of DNA chains from the RNA primers (e.g., as reported by incorporation of labeled deoxyribonucleotide into polynucleotide) relative to the amount of RNA primer formation, is thereby identified as a selective DNA primase potentiator. DNA primase inhibitors find use as commercial reagents and pharmaceutical agents. For example and not limitation, DNA primase inhibitors can be sold and used for inhibiting or controlling DNA replication in mammalian cells, for example, cultured cells in a bioreactor producing a desired bioproduct for industrial or pharmaceutical use. Also for example and not limitation, DNA primase inhibitors can be sold and used in quality control assays to determine the amount of DNA primase in a sample by titration of primase activity with predetermined amounts of the DNA primase inhibitor. Also for example and not limitation, selective DNA primase inhibitors can be sold and used in to quench undesired DNA primase activity in a commercial product, such as an enzyme or polynucleotide preparation (e.g., DNA pol $\alpha$, AMV reverse transcriptase, etc.). DNA primase inhibitors also find use as products which can be manufactured and sold to research laboratories, similar to commercial restriction enzymes and other polynucleotide modifying enzymes which comprise a substantial portion of business activity in the "biotechnology" industry. The DNA primase inhibitors can be used to inhibit mammalian DNA replication in mammalian cells, which is a desired property for certain procedures and experimental protocols; including control of undesired DNA replication in neoplastic cell types, types of virally-infected (e.g., EBV) mammalian cells, hyperplastic conditions, and the like. DNA primase inhibitors are also suitable for use as pharmaceutical agents for inhibiting DNA replication in human pathological conditions, such as neoplasia, hyperplasia, viral infections, and related conditions.

DNA primase potentiators find uses as products as described for inhibitors, supra, but of course potentiate rather than inhibit DNA primase activity. In fact, this is a preferred aspect of the invention. In particular, DNA primase potentiators can be used as pharmaceutical agents or otherwise for enhancing cell proliferation and DNA synthesis in cells, such as cells deficient in primase activity, such as can be the case in certain senescent cell types or conditions.

As an alternative or adjunct to the DNA primase and DNA primase/DNA polymerase activity-based assays, the present invention provides a method for identifying agents which modulate (i.e., potentiate or inhibit) the intermolecular association of mammalian DNA primase and an associated DNA polymerase, typically DNA pol $\alpha$. The method involves determining the capacity of an agent to alter the binding between a mammalian DNA primase and a mammalian DNA polymerase in suitable binding conditions. In one embodiment, at least one of the two binding species (DNA primase and a DNA polymerase) are labeled, and the other binding species is immobilized or provides a basis for immobilization of a bound complex comprising the labeled binding species. In an aspect, a labeled binding species (DNA primase or DNA polymerase) is contacted with an unlabeled binding species (DNA polymerase or DNA primase, respectively) forming a bound labeled complex which is bound to a surface directly, e.g., through a linker, or via an antibody linked to the surface and that specifically binds to the unlabeled component. The amount of bound labeled complex is determined as the amount of label bound to the surface. In an embodiment, a washing step is performed to separate unbound labeled binding species from bound labeled complexes immobilized on the surface. In an alternative embodiment, the physical interaction of the bound labeled complex with the surface is reported, such as where the surface is a fluor or scintillant and the label in the bound labeled complex emits radiation suitable for activating the fluor or scintillant of the surface; light emitted from the surface reports the relative amount of bound labeled complex.

In a variation, immobilization is not required; the DNA primase is labeled with a first fluor which absorbs radiation (particle or wave) and emits phosphorescent or fluorescent light at a first wavelength, the DNA polymerase is labeled with a second fluor which absorbs radiation at said first wavelength and thereby emits fluorescent or phosphorescent radiation at a second wavelength. The labeled DNA primase and DNA polymerase are incubated under suitable binding conditions, and at suitable reactant concentrations whereby the amount of radiation of the second wavelength is approximately proportional to the amount of bound primase/polymerase complexes, and excited with radiation of the first wavelength (or particle type) and the amount of emitted radiation of the second wavelength is detected. The relative amount of radiation of the second wavelength reports the relative amount of bound DNA primase/DNA polymerase complexes. Agents are evaluated to determine their capacity to modulate (i.e., inhibit or potentiate) the intermolecular binding of primase and polymerase in comparison to a control reaction lacking the agent. Active agents can also be tested for their capacity to inhibit DNA primase/DNA polymerase activity in a coupled activity assay as described herein.

The present invention provides a composition comprising a substantially pure protein complex comprising a mammalian DNA primase polypeptide and a mammalian DNA polymerase polypeptide in binding conditions wherein the DNA primase is labeled and the DNA polymerase is immobilized, or wherein the DNA polymerase is labeled and the DNA primase is immobilized. The invention also provides fragments of mammalian DNA primase and mammalian DNA polymerase which retain the ability to bind and form a primase:polymerase complex under physiological or test conditions.

The invention provides screening assays for identifying agents which modulate (e.g., potentiate or inhibit) binding of a human DNA primase polypeptide to a human DNA polymerase polypeptide and/or which modulate (e.g., potentiate or inhibit) binding of a mammalian DNA primase polypeptide to an alternative DNA polymerase-related polypeptide (e.g., human telomerase).

In one embodiment, candidate therapeutic agents are identified by their ability to block the binding of a DNA primase polypeptide to a DNA polymerase polypeptide under binding conditions. Compositions for identifying candidate therapeutic agents typically comprise: (1) a mammalian DNA primase polypeptide capable of binding to a mammalian DNA polymerase polypeptide (e.g., DNA pol $\alpha$), (2) a DNA polymerase which interacts with DNA primase (e.g., DNA pol $\alpha$), (3) aqueous binding conditions (e.g., physiological conditions), and optionally (4) a host cell (e.g., a yeast cell, mammalian cell, bacterial cell), and optionally (5) a reporter polynucleotide or labeled NTP, and optionally (6) a medium to support growth or maintenance of a host cell; an agent is typically added to such a composition for evaluation.

In an embodiment, a candidate therapeutic agent is identified by its ability to block the binding of a mammalian DNA primase fusion polypeptide to a DNA polymerase, fusion polypeptide in a yeast two-hybrid system, wherein the primase fusion polypeptide comprises a primase polypeptide sequence fused to a GAL4 DNA-binding domain vector (GAL4 DB) or a GAL4 activation domain vector (GAL4 AD) and wherein the polymerase fusion polypeptide comprises a polymerase polypeptide sequence fused to a GAL4 activation domain vector (GAL4 AD) or a GAL4 DNA-binding domain vector (GAL4 DB), respectively.

In an embodiment, a candidate therapeutic agent is identified by its ability to block the binding of a primase fusion polypeptide to a polymerase fusion polypeptide in a yeast two-hybrid system, wherein the primase fusion polypeptide comprises a primase polypeptide sequence fused to a GAL4 DNA-binding domain vector (GAL4 DB) or a GAL4 activation domain vector (GAL4 AD) and wherein the polymerase fusion polypeptide comprises a polymerase polypeptide sequence fused to a GAL4 activation domain vector (GAL4 AD) or a GAL4 DNA-binding domain vector (GAL4 DB), respectively.

The invention also provides methods for identifying polypeptide sequences which bind to a DNA primase polypeptide. For example, a yeast two-hybrid screening system can be used for identifying polypeptide sequences that bind to DNA primase. Yeast two-hybrid systems wherein one GAL4 fusion protein comprises a DNA primase polypeptide sequence, typically a full-length of near full-length human DNA primase polypeptide sequence, and the other GAL4 fusion protein comprises a cDNA library member can be used to identify cDNAs encoding proteins which interact with the DNA primase polypeptide, can be screened according to the general method of Chien et al. (1991) Proc. Natl. Acad. Sci. (USA) 88: 9578. Alternatively, an E. coli/BCCP interactive screening system (Germino et al. (1993) Proc. Natl. Acad. Sci. (U.S.A.) 90: 933; Guarente L (1993) Proc. Natl. Acad. Sci. (U.S.A.) 90: 1639) can be used to identify interacting protein sequences. Also, an expression library, such as a γgt11 cDNA expression library, can be screened with a labelled DNA primase polypeptide to identify cDNAs encoding polypeptides which specifically bind to the DNA primase polypeptide. For these procedures, cDNA libraries usually comprise mammalian cDNA populations, typically human, mouse, simian, or rat, and may represent cDNA produced from RNA of one or more cell types, tissues, or organs at any of a variety of developmental stage(s). Specific binding for screening cDNA expression libraries is usually provided by including one or more blocking agent (e.g., albumin, nonfat dry milk solids, etc.) prior to and/or concomitant with contacting the labeled DNA primase polypeptide (and/or labeled anti-DNA primase antibody).

The invention also provides antisense polynucleotides complementary to polynucleotides encoding DNA primase polypeptide sequences and methods for identifying compounds comprising such nucleobase sequences that modulate DNA primase activity. Such antisense polynucleotides are employed to inhibit transcription and/or translation of the DNA primase polypeptide mRNA species and thereby effect a reduction in the amount of the respective DNA primase polypeptide in a cell (e.g., a neoplastic cell of a patient). The DNA primase antisense polynucleotides are typically ssDNA, ssRNA, methylphosphonate backbone nucleic acids, phosphorothiolate backbone nucleic acids, polyamide nucleic acids, and the like antisense structures known in the art. In one aspect of the invention, an antisense polynucleotide is administered to inhibit transcription and/or translation of DNA primase in a human immortal cell.

The present invention also provides a method for diagnosing a disease (e.g., neoplasia, preneoplasia, senescence) in a human patient, wherein a diagnostic assay of human DNA primase activity as described herein is used to determine if a predetermined pathognomonic DNA primase activity level is present in a biological sample from a human or other patient; if the assay indicates the presence of DNA primase activity outside of the normal range or level (e.g., within the predetermined pathognomonic activity range), the patient is diagnosed as having a disease condition or predisposition.

The invention also provides therapeutic agents which inhibit neoplasia or cell replication by modulating function of DNA primase by inhibiting or augmenting formation of complexes of DNA primase:DNA polymerase or of DNA primase with other primase-binding polypeptides; such agents can be used as pharmaceuticals. Such pharmaceuticals will be used to treat a variety of human and veterinary diseases, such as for example and not limitation: neoplasia, hyperplasia, benign prostatic hypertrophy, fibrocystic breast disease, reperfusion injury, myocardial infarction, stroke, traumatic brain injury, neurodegenerative diseases, aging, ischemia, toxemia, infection, autoimmune diseases, AIDS, hepatitis, and the like.

In one aspect, the invention provides methods of identifying DNA primase modulating agents by monitoring a heterodimerization assay. In the assay, a reaction mixture which includes (1) a DNA primase polypeptide capable of binding to a DNA polymerase species, (2) a DNA polymerase capable of binding to said DNA primase polypeptide under binding conditions, and (3) an agent is monitored for the ability of the agent to; inhibit heterodimerization of the DNA primase polypeptide species to the DNA polymerase. Agents which inhibit said heterodimerization are DNA primase modulating agents. These DNA primase modulating agents can modulate apoptosis, cell proliferation, senescence, and/or cell differentiation. Such DNA primase modulating agents can serve as pharmaceuticals, commercial laboratory reagents, and solutes, among other uses.

The invention also provides diagnostic methods involving the use of a human DNA primase assay to diagnose and/or assist in the treatment of disease, such as cancer, and/or to identify pharmaceutical agents which can be used to treat cancer.

A further understanding of the nature and advantages of the invention will become apparent by reference to the remaining portions of the specification.

DETAILED DESCRIPTION

Definitions

Figure 1D:
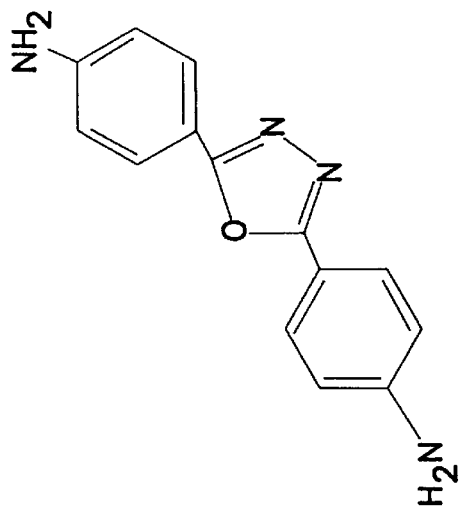
FIG. 1 provides the chemical formulas for example primase modulators.

An "activity" for a primase enzyme refers to a reaction mediated by the enzyme. This includes enzymatic synthesis of polynucleotides by the primase molecule (optionally in the presence of a polymerase), binding of the primase enzyme to a second molecule (e.g., a polymerase molecule) and the like. This activity may be measured directly, e.g., by monitoring incorporation of labeled nucleotides into a polynucleotide synthesized as a result of primase activity or formation of a primase-polymerase binding complex, or indirectly, e.g., by monitoring binding of probes to polynucleotides synthesized as a result of primase activity, or primase dependent cell viability (e.g., in a two hybrid system discussed below), or the like.

As used herein, the term "DNA primase" refers to the mammalian DNA primase proteins designated generally in the art as p49 and p58, including isoforms thereof, unless otherwise stated; human and murine primase proteins and genes are preferred exemplifications of mammalian DNA primase. In one embodiment, an example DNA primase has substantial similarity to the reported sequences of the human and mouse p49 and p58 proteins. This substantial similarity is often at least 85 percent substantially identical to such reported sequences or are at least 90–95 percent substantially identical to the reported sequences, which can be found, for example in the following sources: for mouse primase: Prussak et al. (1989) *J. Biol. Chem.* 264: 4957; Stadlbauer et al. (1994) *Eur. J. Biochem.* 222: 781; Miyazawa et al. (1993) *J. Biol. Chem.* 268: 8111; and for human primase: Stadlbauer et al. (1994) op.cit; Miyazawa et al. (1993) op.cit and such sequences are also reported in the EMBL/GenBank computer-accessible public databases, or commercially available proprietary databases among others.

The term "agent" is used herein to denote a chemical compound (including, but not limited to, organic molecules, polynucleotides, proteins, peptides and the like), a mixture of chemical compounds, an array of spatially localized compounds (e.g., a peptide array, polynucleotide array, and/or combinatorial small molecule array; where "array" refers to a collection of different molecular species immobilized on a surface), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in the described screening assays. Agents are evaluated for potential activity as primase modulators. Naturally occurring nucleotides, template polynucleotides, and ATP, all of which are reactants in the primase reaction, are not agents for the purposes of this invention.

The term "protein interaction modulator" is used herein to refer to an agent which can be identified by one or more screening method(s) of the invention as an agent which selectively modulates protein-protein binding between a first interacting polypeptide and a second interacting polypeptide, typically between primase and a second molecule. Some protein interaction modulators have therapeutic potential as drugs for human use and/or serve as commercial reagents for laboratory research or bioprocess control.

The term "antineoplastic agent" is used herein to refer to agents that have the functional property of inhibiting a development or progression of a neoplasm in a human.

As used herein, the terms "label" or "labeled" refers to incorporation of a detectable marker, e.g., by incorporation of a radiolabel in a nucleotide or amino acid or by attachment to a polypeptide or polynucleotide of biotinyl moieties that can be detected by marked avidin (e.g., streptavidin containing a fluorescent marker or enzymatic activity that can be detected by optical or calorimetric methods). Various methods of labeling polypeptides and glycoproteins as well as nucleotides and polynucelotides are known in the art and may be used. Examples of labels for polypeptides include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide, epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance or impact on other useful or desired properties.

As used herein, "substantially pure" means an object species is a predominant species present (i.e., on a molar basis it is more abundant than any other individual macromolecular species in the composition, other than solvent, carrier, or other non-interfering substance), and preferably a substantially purified fraction is a composition wherein the object species comprises at least about 50 percent (on a molar basis) of all relevant macromolecular species present. Generally, a substantially pure composition will comprise more than about 80 to 90 percent of all macromolecular species present in the composition. Most preferably, the object species is purified to essential homogeneity (designated contaminant species cannot be detected in the composition by conventional detection methods) wherein the composition consists essentially of a single macromolecular species. Solvent species, small molecules (<500 Daltons), and elemental ion species are not considered macromolecular species.

As used herein the terms "pathognomonic activity level" refers to a concentration, amount, or measured enzyme activity, respectively, of a mammalian DNA primase protein or primase/polymerase complex in a sample, that indicates the presence of a pathological (e.g., neoplastic, senescent, immunodeficient, neurodegenerative, inflammatory, etc.) condition or a predisposition to developing a neoplastic disease, such as carcinoma, sarcoma, or leukemia. For purposes of the invention, such levels include any level necessary for the survival of a cell, such as a cancer cell, deleterious to the host organism. A pathognomonic activity is a level in a cell or cellular sample that falls outside the range of normal clinical values that is established by prospective and/or retrospective statistical clinical studies. In an individual having a neoplastic disease (e.g., carcinoma, sarcoma, or leukemia) neoplastic cells can often exhibit an amount of DNA primase protein or mRNA in a cell or tissue sample that is outside the range of concentrations that characterize normal, undiseased individuals; typically the pathognomonic activity is at least about one standard deviation outside the mean normal value, more usually it is at least about two standard deviations or more above the mean normal value. Clinical diagnostic tests can produce some percentage of false positives and false negatives. The sensitivity and selectivity of the diagnostic assays of the invention can be adjusted to satisfy the diagnostic objective and any relevant regulatory requirements of the particular application. In general, diagnostic methods of the invention are used to identify individuals as having a disease, and provide an additional parameter in a differential diagnosis of disease made by a competent health professional. However, it is noted that certain cancer cells can have substantially the same, substantially more, or substantially less DNA primase activity than a similar non-cancerous cell; nonetheless, DNA primase inhibitors would be suitable to treat such cancers.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription reaction mixtures are generally physiological conditions. In general, in vitro physiological conditions comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or: metal chelators; nonionic detergents; membrane fractions; antifoam agents; and/or scintillants.

As used herein, the terms "interacting polypeptide segment" and "interacting polypeptide sequence" refer to a portion of a protein (naturally-occurring or hybrid) which can form a specific binding interaction with a portion of a second protein under suitable binding conditions. Generally, a portion of the first protein preferentially binds to a portion of the second protein forming a heterodimer or higher order heteromultimer comprising the first and second hybrid proteins; the binding portions of each hybrid protein are termed interacting polypeptide segments. Generally, interacting polypeptides can form heterodimers with a dissociation constant ($K_D$) of about $1 \times 10^3$ $M^{-1}$, usually about $1 \times 10^4$ $M^{-1}$, typically about $1 \times 10^5$ $M^{-1}$, preferably at least $1 \times 10^6$ $M^{-1}$ to $1 \times 10^7$ $M^{-1}$ or less, under suitable physiological conditions.

The term "recombinant" as used herein refers to a polypeptide (e.g., DNA primase and/or DNA polymerase) produced by recombinant DNA techniques wherein the gene coding for protein is cloned by recombinant DNA technology. For example, the human gene for DNA primase may be inserted into a suitable DNA vector, such as a bacterial vector or eukaryotic host cell expression vector, and the vector used to transform a suitable host. The gene is then expressed in the host to produce the recombinant protein or other product. The transformed host may be prokaryotic or eukaryotic, including mammalian, yeast, Aspergillus and insect cells. One preferred embodiment employs bacterial cells as the host.

The term "naturally-occurring" as used herein as applied to an object refers to the fact that an object can be found in nature. For example, a polypeptide or polynucleotide sequence that is present in an organism (including viruses) that can be isolated from a source in nature and which has not been otherwise intentionally modified by man in the laboratory is naturally-occurring. Generally, the term naturally-occurring refers to an object as present in a non-pathological (undiseased) individual, such as would be typical for the species.

Cell Proliferation Control and Neoplasia

Many pathological conditions result, at least in part, from aberrant control of cell proliferation, differentiation, and/or cell division, which requires DNA replication. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes, leading to undesired cell proliferation.

The precise molecular pathways and secondary changes leading to malignant transformation for many cell types is not completely clear. However, for cells to replicate and form viable progeny it is essential that DNA replication occur. Thus, it is desirable to identify agents which can modify the activity(ies) of the replicative proteins involved in DNA replication so as to be able to modulate cell proliferation, differentiation, and/or apoptosis for therapeutic or prophylactic benefit. Further, such agents can serve as commercial research reagents for control of cell proliferation, differentiation, and/or apoptosis in experimental applications, and/or for controlled proliferation and differentiation of predetermined cells (e.g., hematopoietic stem cell populations) in vitro, in ex vivo therapy, or in vivo.

Despite progress in developing more defined models of the molecular mechanisms underlying the transformed phenotype and neoplasia, few significant therapeutic methods applicable to treating cancer beyond conventional surgery, radiation, and chemotherapy have resulted. DNA primase modulating agents can provide novel chemotherapeutic agents for treatment of neoplasia, lymphoproliferative conditions, arthritis, inflammation, autoimmune diseases, and the like. Moreover, the ability to screen for such compounds is of immediate commercial benefit to pharmaceutical and drug discovery companies.

DNA Primase and Polymerase Polypeptides and Polynucleotides

The nomenclature used herein, reagents and laboratory procedures in cell culture, molecular genetics, and nucleic acid chemistry and hybridization utilized in the practice of the invention involve certain procedures known and commonly employed in the art.

The known full coding sequences for murine and human DNA primase subunits and DNA polymerase proteins make possible the construction and isolation of polynucleotides that can direct the expression of recombinant DNA primase and polymerase, fragments thereof, or analogs thereof. In addition, primase activity is found in nuclear extracts from cells, e.g., prepared by isolation of the cellular nuclei and lysis of the nuclei. Nuclei are isolated by known techniques, including cell lysis, centrifugation and the like.

Polynucleotides encoding full-length DNA primase or fragments or analogs thereof, may include sequences that facilitate transcription (expression sequences) and translation of the coding sequences, such that the encoded polypeptide product is produced. Construction of such polynucleotides is well known in the art. (see, generally, Sambrook et al. Molecular Cloning: A Laboratory Manual, 2d ed. (1989) Cold Spring Harbor Laboratory Press, Cold Spring Harbor, N.Y. (Sambrook); Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1996 Supplement) (Ausubel).

The nucleic acid compositions used in this invention, whether RNA, DNA, cDNA, genomic DNA, genomic RNA or a hybrid of the various combinations, are isolated from natural sources, cloned heterologous sources, or synthesized in vitro. The nucleic acids are present in transduced or transfected whole cells, in transduced or transfected cell lysates, or in a partially purified or substantially pure form.

In vitro amplification techniques are suitable for amplifying RNA or DNA sequences for use as molecular probes, RNA endonucleases (i.e., where the RNA is a ribozyme) or generating nucleic acids for subsequent subcloning.

Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564.

Oligonucleotides useful as probes in the assays of the invention are synthesized on an automated synthesizer such as an Applied Bio Systems oligonucleotide synthesizer, according to specifications provided by the manufacturer.

Production of anti-DNA Primase or anti-Pol α Antibodies

Native primase and polymerase proteins, fragments thereof, or analogs thereof, may be used to immunize an animal for the production of specific antibodies. These antibodies can comprise a polyclonal antiserum or can comprise a monoclonal antibody produced by hybridoma cells. For general methods to prepare antibodies, see *Antibodies: A Laboratory Manual,* (1988) E. Harlow and D. Lane, Cold Spring Harbor Laboratory, Cold Spring Harbor, N.Y. These antibodies are optionally used to monitor the presence or absence of primase in an assay of the invention.

Yeast Two-Hybrid Screening Assays

The invention provides hybrid screening assays and related host organisms (typically unicellular organisms) which harbor a mammalian DNA primase protein two-hybrid system, typically in the form of polynucleotides encoding a first hybrid protein, a second hybrid protein, and a reporter gene, wherein said polynucleotide(s) are either stably replicated or introduced for transient expression. In an embodiment, the host organism is a yeast cell (e.g., *Saccharomyces cervisiae*) in which the reporter gene transcriptional regulatory sequence comprises a Gal4-responsive promoter.

Yeast comprising (1) an expression cassette encoding a GAL4 DNA binding domain (or GAL4 activator domain) fused to a binding fragment of primase capable of binding to a DNA polymerase polypeptide, (2) an expression cassette encoding a GAL4 DNA activator domain (or GAL4 binding domain, respectively) fused to a member of a cDNA library or a binding fragment of a DNA polymerase capable of binding to a mammalian DNA primase polypeptide, and (3) a reporter gene (e.g., β-galactosidase) comprising a cis-linked GAL4 transcriptional response element can be used for agent screening. Such yeast are incubated with a test agent and expression of the reporter gene (e.g., β-galactosidase) is determined; the capacity of the agent to inhibit expression of the reporter gene as compared to a control culture identifies whether the candidate agent is a DNA primase modulatory agent.

Yeast two-hybrid systems may be used to screen a mammalian (typically human) cDNA expression library, wherein human cDNA is fused to a GAL4 DNA binding domain or activator domain, and either a DNA primase or DNA polymerase polypeptide sequence is fused to a GALA activator domain or DNA binding domain, respectively. Such a yeast two-hybrid system can screen for cDNAs that encode proteins which bind to DNA primase or polymerase sequences. For example, a cDNA library can be produced from mRNA from a human mature B cell (Namalwa) line (Ambrus et al. (1993) *Proc. Natl. Acad. Sci.* (U.S.A.)) or other suitable cell type. Such a cDNA library cloned in a yeast two-hybrid expression system (Chien et al. (1991) *Proc. Natl. Acad. Sci.* (U.S.A.) 88: 9578) can be used to identify cDNAs which encode proteins that interact with primase or polymerase and thereby produce expression of the GAL4-dependent reporter gene. Polypeptides which interact with primase or polymerase can also be identified by immunoprecipitation of primase or polymerase with antibody and identification of co-precipitating species and by screening a peptide library (e.g., a bacteriophage peptide display library, a spatially defined peptide array, and the like) with a primase or polymerase polypeptide.

The construction of yeast two-hybrid systems is generally known. This approach identifies protein-protein interactions in vivo through reconstitution of a transcriptional activator (Fields and Song (1989) *Nature* 340: 245), such as the yeast Gal4 transcription protein. The yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver S C and Hunt S W (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechniques* 14: 920; and Vojtek et al. (1993) *Cell* 74: 205). As applied to the present case, the two-hybrid system permits identification of peptide sequences which interact with primase, and therefore, are potential primase modulators. These potential modulators can be tested for primase modulation in the assays of the invention.

Binding Assays For Detecting Primase-Polymerase Binding Modulators

Administration of an efficacious dose of an agent capable of specifically inhibiting primase:polymerase complex formation to a patient can be used as a therapeutic or prophylactic method for treating pathological conditions (e.g., cancer, inflammation, lymphoproliferative diseases, autoimmune disease, neurodegenerative diseases, and the like) which are effectively treated by modulating DNA replication. Thus, assays which monitor primase-polymerase binding are of value in screening for primase modulators.

Binding assays often take one of two forms: immobilized primase polypeptide(s) can be used to bind labeled polymerase polypeptide(s), or conversely, immobilized polymerase polypeptide(s) can be used to bind labeled primase polypeptides. In each case, the labeled polypeptide is contacted with the immobilized polypeptide under conditions that permit specific binding of the polypeptides(s) to form a complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. Additions, deletions, modifications (such as pH) and substitutions (such as KCl substituting for NaCl or buffer substitution) may be made to these basic conditions. Modifications can be made to the basic binding reaction conditions so long as specific binding of primase polypeptide(s) to polymerase polypeptides occurs in the control reaction(s).

In such reactions, at least one polypeptide species typically is labeled with a detectable marker. Suitable labeling includes, but is not limited to, radiolabeling by incorporation of a radiolabeled amino acid (e.g., $^{14}$C-labeled leucine, $^3$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a primase or polymerase polypeptide may be used in combination with an accessory protein (e.g., a protein which forms a complex with the polypeptide in vivo). It is typically preferred that different labels are used for each polypeptide species, so that binding of individual and/or heterodimeric and/or multimeric complexes can be readily distinguished. For example but not by way of limitation, a primase polypeptide is labeled with fluorescein and an accessory polypeptide is labeled with a fluorescent marker that fluoresces with either a different excitation wavelength or emission wavelength, or both. Alternatively, double-label scintillation counting is used, wherein a primase polypeptide is labeled with one isotope (e.g., $^3$H) and a second polypeptide species is labeled with a different isotope (e.g., $^{14}$C) that can be distinguished by scintillation counting using standard discrimination techniques.

Labeled polypeptide(s) are contacted with immobilized polypeptide(s) under aqueous conditions as described herein. The time and temperature of incubation of a binding reaction is optionally varied, with the selected conditions permitting specific binding to occur in a control reaction where no agent is present. Preferable embodiments employ a reaction temperature of about at least 15 degrees Centigrade, more preferably 30 to 42 degrees Centigrade, and a time of incubation of approximately at least 15 seconds, although longer incubation periods, from 30 seconds to a minute to several minutes or more, are preferable so that, in some embodiments, a binding equilibrium is attained. Binding kinetics and the thermodynamic stability of bound primase:polymerase complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other standard analytic methods (*Proteins, Structures and Molecular Principles,* (1984) Creighton (ed.), W. H. Freeman and Company, New York).

Specific binding of labeled primase or polymerase polypeptide to immobilized polymerase or primase polypeptide, respectively, is determined by including unlabeled competitor protein(s) (e.g., albumin). Similarly, specific binding of labeled primase or polymerase polypeptide to immobilized polymerase or primase polypeptide, respectively, is determined by including unlabeled competitor protein(s) (e.g., albumin). After a binding reaction is completed, labeled polypeptide(s) specifically bound to immobilized polypeptide is detected. For example and not by way of limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a primase polypeptide and a polymerase polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci.* (U.S.A.) 83: 5889). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface (e.g., on a bead) and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a primase polypeptide to a polymerase polypeptide or disrupt, modulate, inhibit, or potentiate the activity of either or both. Agents which, when added to a binding reaction, inhibit formation of primase:polymerase complexes are thereby identified as primase inhibitors; such agents inhibit DNA replication and can be used to inhibit replication of neoplastic cells. Agents which, when added to a binding reaction, enhance formation of primase:polymerase complexes are thereby identified as primase potentiators (e.g., primase agonists; such agents can find use to enhance DNA replicative potential and cell viability, including viability of senescent cell types. In a preferred embodiment, several binding reactions are monitored simultaneously, e.g., using a format which permits simultaneous analysis of several samples (microtiter plates, etc.). In a preferred embodiment, the assays are automated, e.g., using robotics for pipetting samples into microtiter plates.

One means for detecting binding of a primase polypeptide to a polymerase polypeptide is to immobilize the primase polypeptide, such as by covalent or noncovalent chemical linkage to a solid support, and to contact the immobilized primase polypeptide with a polymerase polypeptide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a primase polypeptide to a polymerase polypeptide. Binding of the labeled polymerase polypeptide to the immobilized primase is measured by determining the extent to which the labeled polymerase polypeptide is immobilized as a result of a specific binding interaction. Such specific binding may be reversible, or may be optionally irreversible if a cross-linking agent is added in appropriate experimental conditions.

Agents that inhibit or augment the formation of bound complexes as compared to a control binding reaction lacking agent are thereby identified as primase-modulating agents and are candidate therapeutic agents.

In one variation, the binding assay is performed in vivo in a cell, such as a yeast cell (e.g., Saccharomyces), and agents which inhibit intermolecular binding between a primase protein and a polymerase polypeptide are identified as primase-modulating agents. For example, the in vivo screening assay is optionally a yeast two-hybrid system wherein the yeast cells express: (1) a first fusion protein comprising primase and a first transcriptional regulatory protein sequence (e.g., GAL4 activation domain), (2) a second fusion protein comprising a polymerase polypeptide and a second transcriptional regulatory protein sequence (e.g., GAL4 DNA-binding domain), and (3) a reporter gene (e.g., β-galactosidase, an auxotroph complementing gene) which is transcribed when an intermolecular complex comprising the first fusion protein and the second fusion protein is formed. If a functional primase:polymerase polypeptide complex forms, such as in a control assay lacking agent, the cell expresses the reporter gene which can be detected. Agents which inhibit or augment formation of functional primase:polymerase polypeptide complexes (and thus reporter gene expression) are thereby identified as primase-modulating agents and candidate drugs and commercial cell culture reagents and cell preservatives and the like.

In an embodiment, the physical interaction of the bound labeled complex with the surface is reported, such as where the surface is a fluor or scintillant and the label in the bound labeled complex emits radiation suitable for activating the fluor or scintillant of the surface; light emitted from the surface reports the relative amount of bound labeled complex. A suitable system is the scintillation proximity assay (Amersham), wherein the unlabeled component is bound to a fluor-containing bead. Alternative systems include the "Flash Plate" system (LKB).

In a variation, immobilization is not required; the DNA primase is labeled with a first fluor which absorbs radiation (particle or wave) and emits phosphorescent or fluorescent light at a first wavelength, the DNA polymerase is labeled with a second fluor which absorbs radiation at said first wavelength and thereby emits fluorescent or phosphorescent radiation at a second wavelength. The labeled DNA primase and DNA polymerase are incubated under suitable binding conditions, and at suitable reactant concentrations whereby the amount of radiation of the second wavelength is approximately proportional to the amount of bound primase/polymerase complexes, and excited with radiation of the first wavelength (or particle type) and the amount of emitted radiation of the second wavelength is detected. The relative amount of radiation of the second wavelength reports the relative amount of bound DNA primase/DNA polymerase complexes. An example of suitable system is a dye-dye transfer system (Packard).

Agents are evaluated to determine their capacity to modulate (i.e., inhibit or potentiate) the intermolecular binding of primase and polymerase in comparison to a control reaction lacking the agent. Active agents can then be tested for their capacity to inhibit DNA primase/DNA polymerase activity in a coupled activity assay as described herein.

DNA Primase and Coupled DNA Primase/Polymerase Assays

The DNA primase and primase/polymerase assays employed in the present method can be performed by any suitable method known in the art for measuring mammalian DNA primase and/or coupled primase/polymerase activity. Preferred primase template polynucleotides and reaction conditions (including purification method for obtaining primase and pol α) include, for example, those described in Suzuki et al. (1993) *Biochemistry* 32: 12782; Kuchta et al. (1992) *Biochemistry* 31: 4720; Copeland and Wang (1993) *J. Biol. Chem.* 268: 26179; Harrington and Perrino (1995) *Nucl. Acids Res.* 23; 1003, each incorporated herein by reference. The Examples herein provide additional preferred embodiments.

For example and not limitation, primase reactions optionally comprise the following reaction conditions: 100 pmol of a 40mer DNA template comprising all 4 nucleotides; 20 mM Tris, pH 7.5; 5 mM MgCl2; 2 mM DTT; 0.1 mg/ml BSA; 100 μM each of ATP, CTP, GTP, and UTP, wherein one of the NTPs is labeled at the α phosphate with $^{32}P$; and pol α:primase (0.7U pol α and 6.3U primase). Incubation is typically at 25–42 degrees C., with a preferred temperature being 30–37 degrees C. Incubation times are typically from 0.5 minutes to 60 minutes. Reactions can be conveniently stopped by addition of EDTA to 5 mM final concentration. Following a reaction, the amount of a product polynucleotide is determined by assessing the reaction mixture, e.g., following a suitable incubation period with a substrate which selectively immobilizes or binds to polynucleotides and which substantially does not immobilize or bind to mononucleotides; one example of such a substrate is a charged membrane (e.g., Nylon 66, nitrocellulose, DEAE paper, whatman paper, filter paper, etc.). Alternatively, reaction products can be chromatographed or electrophoresed (e.g., PAGE) to separate polynucleotide products from unincorporated nucleotides. The amount of label incorporated into polynucleotide products report the relative activity of the DNA primase.

For example and not limitation, coupled primase/polymerase reactions can comprise the following reaction conditions: 100 pmol of a linear ssDNA template comprising all 4 nucleotides and being about 450 nt in length; 20 mM Tris, pH 7.5; 5 mM MgCl2; 2 mM ATP; 200 μM CTP, GTP, and UTP; 100 μM dATP, dGTP, dTTP, and 25 μM $^{32}P$-α-dCTP; and pol α:primase (9.3U pol α and 29 primase). Incubation is typically at 25–42 degrees C., with a preferred temperature being about 30–37 degrees C. Incubation times are often 0.5 minutes to 60 minutes. Reactions are conveniently stopped by addition of EDTA to 5 mM final concentration. Following reaction, the amount of product polynucleotide is determined by contacting the reaction mixture, following a suitable incubation period, with a substrate which selectively immobilizes or binds to polynucleotides and which substantially does not immobilize or bind to mononucleotides; one example of such a substrate is a charged membrane (e.g., Nylon 66, nitrocellulose, DEAE paper whatman paper, filter paper, etc.). Alternatively, reaction products can be chromatographed or electrophoresed (e.g., PAGE) to separate polynucleotide products from unincorporated nucleotides. The amount of label incorporated into polynucleotide products report the relative activity of the DNA primase.

Compound Chemistry

Figure 1D:
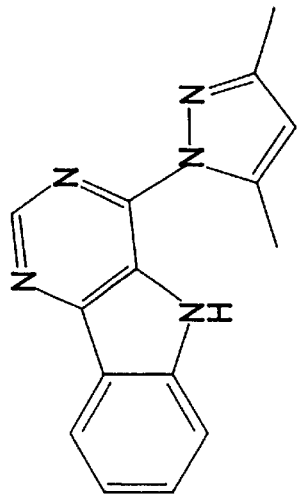
Figure 1D:
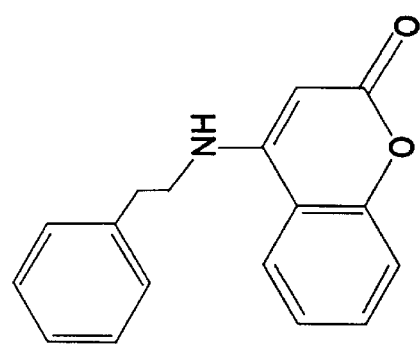
Figure 1D:
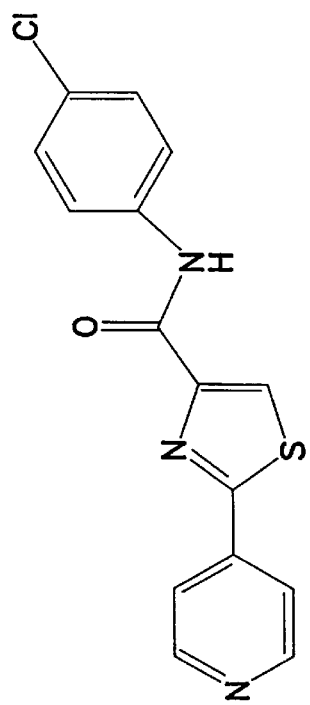
Figure 1D:
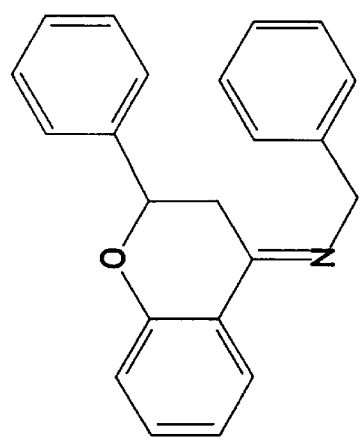

The invention provides several example primase modulators. The primase modulator compounds shown in FIG. 1 are easily synthesized by one of skill using widely available compounds, given the structure of the particular modulator, using standard synthetic techniques. A guide to standard synthetic organic chemistry is found in March, Advanced Organic Chemistry Reactions, Mechanisms and Structure 4th ed J. Wiley and Sons (New York, 1992) and the references cited therein. Furthermore, one of skill will recognize that additional primase modulators are easily synthesized by reference to the given primase modulators by minor modification of the example modulators.

For example, alkyl groups (branched or unbranched, saturated or unsaturated, monovalent hydrocarbon radical having from 1–12 carbons) can be substituted for one another. Substituted alkyls (an alkyl having one or more functional group such as a lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like) are also substituted for one another using standard synthetic methods. Aryls (aromatic substituents such as single or multiple aromatic rings which are fused together, linked covalently, or linked to a common group such as a methylene or ethylene moiety) can be substituted at similar positions in the given primase modulators. Typical aromatic ring(s) may include phenyl, naphthyl, biphenyl, diphenylmethyl and benzophenone among others. Similarly, substituted aryls, including an aryl and including one or more functional group such as a lower alkyl, acyl, halogen, alkylhalos, hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety are optionally substituted for one another using available techniques. Acyl groups with ketone substituents, —C(O)R, where R is alkyl or substituted alkyl, aryl or substituted aryl are also substituted for one another. Halogens, including fluorine, bromine, chlorine and iodine atoms are substituted at similar positions on the given modulators to yield functionally similar molecules. Hydroxy groups (OH) are optionally substituted with primary amines (R—$NH_2$) or Alkoxy groups (an —OR group, where R is a lower alkyl, substituted lower alkyl, aryl, substituted aryl, arylalkyl or substituted arylalkyl. Alkylamino groups are substituted, in which secondary and tertiary amines wherein the alkyl groups may be either the same or different and may consist of straight or branched, saturated or unsaturated hydrocarbons are substituted for one another. Mercapto groups having the general structure R—S—R' wherein R and R' are the same or different and are alkyl, aryl or heterocyclic as described herein are optionally subsituted for one another. Saturated cyclic hydrocarbons such as cyclopropyl, cyclobutyl, cyclopentyl, etc., and substituted analogues of these structures are optionally substituted for one another. Unsaturated cyclic hydrocarbons (a monovalent non-aromatic group with at least one double bond, such as cyclopentene, cyclohexene, etc. and substituted analogues thereof are optionally substituted for one another in the modulators of the invention. Heteroaryl groups having aromatic rings in which one or more carbon atoms of the aromatic ring(s) are substituted by a heteroatom such as nitrogen, oxygen or sulfur with a single aromatic ring, multiple aromatic ring(s), or one or more aromatic rings coupled to one or more non-aromatic ring(s) can be substituted for one another using standard organic chemical synthetic methods. In structures having multiple rings, the rings can be fused together, linked covalently, or linked to a common group such as a methylene or ethylene moiety. Substituted heteroaryl groups having one or more functional group such as lower alkyl, acyl, halogen, alkylhalos (e.g. $CF_3$), hydroxy, amino, alkoxy, alkylamino, acylamino, acyloxy, mercapto, etc. are optionally substituted for one another. Heterocyclic groups having a monovalent saturated or unsaturated non-aromatic group having a single ring or multiple condensed rings from 1–12 carbon atoms and from 1–4 heteroatoms selected from nitrogen, sulfur or oxygen within the ring are optionally substituted for one another. All of these substitutions to the example modulators are performed using standard synthetic techniques, and it will be appreciated that many conservatively substituted (i.e., by substituting the example modulators with groups having similar functionality as described) primase modulators are commercially available.

The foregoing description of the preferred embodiments of the present invention has been presented for purposes of illustration and description. They are not intended to be exhaustive or to limit the invention to the precise form disclosed, and many modifications and variations are possible in light of this teaching.

EXAMPLES

The following examples are provided by way of illustration only and not by way of limitation. Those of skill will readily recognize a variety of noncritical parameters which can be changed or modified to yield similar results.

Example 1

Primase Activity

A. Nuclear Extraction of Primase

In one embodiment, the present invention utilizes a nuclear extract to obtain primase enzyme, using a CHAPS nuclear extract protocol. In one embodiment, Hek 293 cells were used as a source of cells for preparation of nuclei.

HEK 293 cells are an adenovirus-transformed human embryonic kidney cell line. These cells grow readily in suspension cultures with an optimal harvest density of $0.5 \times 10^9$ cells per liter and doubling time of 24 hours. A commercial supplier, Cellex, maintains 293 suspension cultures in spinner flasks, and provides a weekly supply of $2 \times 10^{11}$ cells (from 400 liters of culture). Done by Cellex on a weekly basis, the 293 cells were harvested, washed twice in PBS (Ca/Mg free), snap frozen as a wet cell pellet, and shipped on dry ice to Geron Corp. (frozen cells were stored at $-80°$ C.). A weekly supply comes as eight 250 ml polypropylene centrifuge bottles, each containing about 75 ml of packed cells. It will be appreciated that many mammalian cells, both naturally occurring and cells in culture can be substituted for Hek 293 cells in the protocols of the invention to supply primase.

In the CHAPS nuclear extract protocol, 5 volumes of wash buffer (10 mM HEPES, pH 7.5, 1.5 mM $MgCl_2$, 10 mM KCL, 1 mM DTT) was added to 1 volume of packed cells. The cells were partially mixed in the wash buffer using gentle mixing to avoid lysis of the cells. The cells were pelleted by centrifugation at 1780×g for 10 minutes at 4° C. The supernatant was discarded and 5 volumes of lysis buffer (10 mM Tris HCL, pH 7.5, 1 mM MgCl$_2$, 1 mM EGTA, 0.5% CHAPS (Pierce catalogue number 28299), 0.1 mM PMSF, 5 mM 2-mercaptoethanol, 10% glycerol, 1 mM Benzamide (Sigma catalogue number B6506) and 1 mM Na Metabisulfate (Sigma catalogue number S1516)) was added to 1 volume of cell pellet. The cells were completely resuspended by stirring and pipetting to break apart the pellet. At 20 minutes after beginning resuspension, the mixture was pelleted by centrifugation at 1780×g for 10 minutes at 4° C., resulting in pelleting of the nuclei. The supernatant was poured off into an ultracentrifuge tube and centrifuged in an SW28 rotor at 27,500 rpm (approximately 100,000×g) for 33 minutes at 4° C.

To prepare a nuclear extract, the nuclei were resuspended in 0.5 volumes of nuclear extract buffer (20 mM HEPES pH 7.9, 20 mM NaCl, 1.5 mM MgCl$_2$, 0.5 mM EGTA, 25% glycerol, and, added just before use, 1 mM DTT, 0.1 mM PMSF, 1 mM sodium metabisulfite and 1 mM Benzamidine). While vortexing, 0.5 volumes of nuclear extract buffer containing 1.2 M NaCl was added. The mixture was dounce homogenized, placed on ice and stirred for at least 30 minutes. The mixture was then spun for 75 minutes at 18,000 rpms in an SS34 rotor. The supernatant was dialyzed overnight, or twice for two hours each time against hypo buffer having 100 mM NaCl. Insoluble material was spun out and the supernatant snap frozen in liquid nitrogen.

B. Isolation of Recombinant Primase

Recombinant primase was isolated from *E. coli.*, essentially as taught by Copeland et al (1993) *J. Biol. Chem.* 268(35):26179–26189.

Example 2

A Primase Assay

A high throughput primase assay measuring primase activity by incorporation of radioactive nucleotides is described.

In the assay, primase was diluted with primase dilution buffer (50% glycerol, 50 mM Tris HCl (pH 8.0) 20 mM KCl, 1 mM EDTA, 1 mM βME) to achieve a selected reaction volume (typically, reactions were carried out in an overall volume of 60 μl). A typical 60 μl reaction volume further included 50 mM Tris HCl (pH 8.0); 20 mM KCl, 200 μg/ml BSA, 4 mM MgCl$_2$, 2 mM fresh DTT, 2 mM rATP, 5 uCi $^{32}$P (800 Ci/mmol) or 2.5 μCi $^{33}$P (2,000 Ci/mMol) dATP, 10 ug/ml Poly (dT), and primase and polymerase α.

The recombinant 180 Kd human polymerase α protein was isolated from a bacculovirally transduced SF9 cell as described in Wang et al. (1995) *Methods in Enzymology* 262: 77–84. Typically, about 0.05 μg of p180 and about 0.025 μg of a 1:1 mixture of p49/p58 primase subunits were used per reaction.

Several reactions were typically set up in parallel, although a single reaction can also be assessed. For example, a Zymate XP (Zymark Corporation; Hopkinton, Mass.) automated robot using Microlab 2200 (Hamilton; Reno, Nev.) pipeting station to transfer parallel samples to 96 well microtiter plate was used to set up several parallel simultaneous reactions.

Parallel reactions were incubated for 30 minutes at 30° C. 15 μl of each reaction was spotted into one well on a Unifilter plate (Whatman GF/C glass fiber filter bottom), typically using the automated system described. The filters were then air dried. The Unifilter plate was placed onto the vacuum chamber of a dot blot apparatus, and 200 μl of ice cold 5% TCA/20 mM sodium pyrophosphate wash was added to each well, and vacuum applied. Each filter was washed three times. 100 μl of an ice cold 70% ethanol wash was added then added to each well, and vacuum applied. The ethanol wash was repeated, and the filters allowed to air dry. Excess fluid was removed from the bottom of the plate. The bottom of the plate was sealed with a transparent sealer, and 50 μl of Microscint-20 scintillation fluid was added to each well, e.g., using a Biomek1000® (Beckman Instruments; Dallas, Tex.). The top of the plate was sealed with TOPSEAL-S® Microplate Heat Sealing Film and CPM were counted for each well using a topcount microplate scintillation counter (Packard; Downers Grove, Ill.) or Trilux Microbeta 1450 (Wallac; Gaithersburg, Md.).

Certain reagents useful in the primase activity assays of these example are also described in Copeland et al. *J. Biol. Chem.* 268(35) 26179–26189.

Example 3

A Primase Assail Using Nuclear Extract as A Source for Primase Activity

An assay similar to Example 2 was also developed to measure primase activity. Although the assay is described below with reference to using a nuclear extract as the source for primase activity, one of skill will recognize that the assay can easily be adapted for purified or recombinant primase. Examples 1 and 2 provide a description of the buffers, nuclear extracts, etc.

| Stock | Final | Amount/Reaction (μl) |
|---|---|---|
| 10 x RPB | 1 x | 6 |
| 20 mM rATP | 2 mM | 6 |
| $^{32}$P dATP (2000 Ci/mmol) | 2.5 μCi | .25 |
| 200 ug/ml | 10 μg/ml | 3 |
| Nuclear Extract | 6 μg | .5 |
| Dep C H$_2$O | | 44.25 |

The reagents were combined into one or more separate reaction mixtures, with the poly dT, nuclear extract, and $^{32}$dATP being added just before use. The reaction mixtures were incubated for 1 hour at 37° C. The reactions were spotted onto filters on a unifilter plate and treated as described in Example 2.

Example 4

Primase Modulators

The primase modulator compounds show in FIG. 1 were determined to modulate primase activity in the assays shown above, using a nuclear extract comprising primase activity, as described above.

For primary screening, compounds were added at the beginning of the reaction with all reagents as described above. Compounds were tested at a concentration of 100 μM. Compounds were tested in duplicate reactions.

To measure the concentration response for compounds which showed primase modulation, compounds were tested in duplicate at 100 μM, 32 μM, 10 μM, and 3.2 μM. This concentration information was used to determine the approximate IC50 for the primase modulating agents described in FIG. 1. The extract/enzyme preparation for primase modulating agents was preincubated with the compound for 30 min at 37° C. prior to addition of the remaining reagents.

The example modulators are primase inhibitors. The IC50s for the compounds indicated in FIG. 1 was the approximate concentration of the modulator at which 50% of the primase enzyme activity in a reaction mixture was inhibited by the modulator.

The particular primase modulator compounds shown in FIG. 1 are easily synthesized by one of skill using available compounds, given the structure of the particular modulator. A guide to standard synthetic organic chemistry is found in March, Advanced Organic Chemistry Reactions, Mechanisms and Structure 4th ed J. Wiley and Sons (New York, 1992). One of skill will recognize that additional primase modulators are easily synthesized by reference to the given primase modulators by minor modification of the example modulators, as described supra.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Such modifications and variations which are apparent to a person skilled in the art are intended to be within the scope of the following claims to this invention.

What is claimed is:

1. A method for identifying an agent which inhibits a mammalian DNA primase activity, said method comprising:

providing a cell comprising a mammalian DNA primase enzyme;

contacting the cell with the agent; and, measuring the activity of the primase enzyme, whereby a decrease in the measured activity of the primase enzyme in the presence of the agent indicates that the agent inhibits primase activity.

2. The method of claim 1, further comprising measuring the activity of the primase enzyme by monitoring incorporation of a nucleotide label into a nucleic acid polymer, which polymer is synthetically primed by the primase enzyme.

3. The method of claim 1, further comprising measuring the activity of the primase enzyme by measuring the binding of the enzyme to a polymerase protein.

4. The method of claim 1, further comprising comparing the activity of the primase enzyme in the presence of the agent to an activity of the primase enzyme in the absence of the agent.

5. The method of claim 1, wherein the agent produces a statistically significant decrease in the relative amount of incorporated label as compared to the relative amount of incorporated label in a parallel reaction lacking the agent, thereby determining that the agent is a primase inhibitor.

6. The method of claim 1, further comprising measuring the production of a nucleic acid molecule, which molecule is primed by the mammalian primase enzyme, wherein the molecule is selected from the group consisting of DNA and RNA, whereby measuring the production of the nucleic acid molecule provides an activity measurement for the mammalian primase enzyme.

7. The method of claim 1, wherein the cell further comprises polymerase α, and the method further comprises measuring the production of a DNA molecule, which molecule is primed by the mammalian primase enzyme and synthesized by polymerase α.

8. The method of claim 1, further comprising hybridizing a probe to a primase reaction product, thereby determining the activity for the primase enzyme.

9. The method of claim 1, further comprising hybridizing a probe polynucleotide to a primase reaction product, thereby determining the activity for the primase enzyme, wherein the probe polynucleotide is immobilized on a solid surface, wherein the solid surface is optionally washed to remove non-specifically bound components, and is optionally treated with a blocking agent selected from the group consisting of albumin, a nonfat milk protein, polyvinyl pyrrolidone, and Ficoll.

10. The method of claim 1, wherein the cell comprising the primase enzyme is contacted by the agent in a microtiter plate, and the activity of the primase enzyme is measured on a glass fiber filter.

11. The method of claim 1, wherein the mammalian primase is produced by recombinant expression in the cell.

12. A method of inhibiting the activity of a mammalian primase, comprising contacting a cell comprising the primase with an agent which inhibits mammalian primase activity identified according to the method of claim 1.

* * * * *

```
                         SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primase template
              polynucleotide"

(xi) SEQUENCE DESCRIPTION: SEQ ID NO:1:

GCTTTCTTC                                                              9

(2) INFORMATION FOR SEQ ID NO:2:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primase template
              polynucleotide"

(xi) SEQUENCE DESCRIPTION: SEQ ID NO:2:

GCTTTCTTCC                                                            10
```